(12) United States Patent
Shen et al.

(10) Patent No.: US 10,500,281 B2
(45) Date of Patent: Dec. 10, 2019

(54) INJECTABLE LONG-ACTING LOCAL ANESTHETIC SEMI-SOLID FORMULATIONS AND ITS COMPOSITIONS

(71) Applicant: Mira Pharma Corporation, Kenmore, WA (US)

(72) Inventors: Hui Rong Shen, Bothell, WA (US); Na Gan, Bothell, WA (US)

(73) Assignee: Mira Pharma Corporation, Kenmore, WA (US)

( * ) Notice: Subject to any disclaimer, the term of this patent is extended or adjusted under 35 U.S.C. 154(b) by 0 days.

(21) Appl. No.: 14/839,352

(22) Filed: Aug. 28, 2015

(65) Prior Publication Data

US 2015/0366967 A1  Dec. 24, 2015

Related U.S. Application Data

(63) Continuation of application No. PCT/US2014/019704, filed on Feb. 28, 2014.

(60) Provisional application No. 61/771,011, filed on Feb. 28, 2013.

(51) Int. Cl.
  *A61K 47/14* (2017.01)
  *A61K 31/445* (2006.01)
  *A61K 9/00* (2006.01)

(52) U.S. Cl.
  CPC ............ *A61K 47/14* (2013.01); *A61K 9/0019* (2013.01); *A61K 31/445* (2013.01)

(58) Field of Classification Search
  CPC .............................. A61K 47/14; A61K 31/445
  See application file for complete search history.

(56) References Cited

U.S. PATENT DOCUMENTS

| | | |
|---|---|---|
| 6,214,387 B1 | 4/2001 | Berde et al. |
| 6,521,259 B1 | 2/2003 | Chasin et al. |
| 6,613,355 B2 | 9/2003 | Ng et al. |
| 6,790,458 B2 | 9/2004 | Ng et al. |
| 6,861,068 B2 | 3/2005 | Ng et al. |
| 6,921,541 B2 | 7/2005 | Chasin et al. |
| 7,053,209 B1 | 5/2006 | Gibson et al. |
| 7,666,914 B2 | 2/2010 | Richlin et al. |
| 8,182,835 B2 | 5/2012 | Kim et al. |
| 8,221,778 B2 | 7/2012 | Siegel et al. |
| 2004/0001889 A1 | 1/2004 | Chen et al. |
| 2007/0184089 A1* | 8/2007 | Howie ............... A61K 9/0051 424/427 |
| 2015/0297729 A1 | 10/2015 | Ottoboni et al. |

FOREIGN PATENT DOCUMENTS

| | | | |
|---|---|---|---|
| CN | 102458388 A | 5/2012 | |
| CN | 102858374 A | 1/2013 | |
| CN | 102869344 A | 1/2013 | |
| CN | 102892408 A | 1/2013 | |
| DE | 10033059 A1 | 1/2002 | |
| JP | S62-045538 A | 1/1987 | |
| JP | H07-508708 A | 9/1995 | |
| JP | H08-143449 A | 6/1996 | |
| JP | 2001-261558 A | 9/2001 | |
| JP | 2004-501185 A | 1/2004 | |
| JP | 2004-506697 A | 3/2004 | |
| JP | 2007-521225 A | 8/2007 | |
| JP | 2009-518374 A | 5/2009 | |
| JP | 2010-522738 A | 7/2010 | |
| KR | 10-2012-0046155 A | 5/2012 | |
| WO | WO 1993/019736 A1 | 10/1993 | |
| WO | WO 1997/044021 A1 | 11/1997 | |
| WO | WO 2002/000203 A1 | 1/2002 | |
| WO | WO 2002/015937 A2 | 2/2002 | |
| WO | WO 2007/066148 A1 | 6/2007 | |
| WO | WO 2007066148 A1 * | 6/2007 | ........... A61K 9/0014 |
| WO | WO 2008/117268 A2 | 10/2008 | |
| WO | WO 2010/142457 A1 | 12/2010 | |
| WO | WO 2010142457 A1 * | 12/2010 | ........... A61K 9/0031 |
| WO | WO 2011/075623 A1 | 6/2011 | |
| WO | WO 2011/121034 A2 | 10/2011 | |
| WO | WO 2011/121082 A1 | 10/2011 | |
| WO | WO 2014/134586 A2 | 9/2014 | |

OTHER PUBLICATIONS

Larsen et al.; "Assessment of Drug Release from Oil Depot Formulations Using an In Vitro Model-Potential Applicability in Accelerated Release Testing"; 2008; Drug Development and Industrial Pharmacy; 34:297-304.*

Cognis, Nutrition & Health; Product Datasheet: Myritol® 318 PH; https://e-applications.basf-ag.de/data/basf-pcan/pds2/pds2-web.nsf/8C45C964E30F90BDC12573B100597C06/$File/MYRITOL_r__318_PH_E.pdf; accessed Oct. 16, 2016.*

Juárez-Soberanez et al.; "Gelucire 39/01 As Excipient for Gastroretentive Metronidazole Sustained Delivery"; 2011; International Journal of Pharmacy and Pharmaceutical Sciences; vol. 3, (Suppl 2): 86-91.*

Zausig et al.; "Lipophilicity of local anesthetics and success of lipid emulsion therapy"; 2012; Crit. Care Med; 40(1):359-360.*

Larsen et al. ("Characteristics of drug substances in oily solutions. Drug release rate, partitioning and solubility"; 2002; International Journal of Pharmaceutics; 232: 107-117.*

Cremer Care; "Softigen 701"; http://www.petercremerna.com/products/657474081; accessed Sep. 26, 2017.*

Sokolsky-Papkov et al.; "Prolonged Local Anesthetic Action Through Slow Release from Poly (Lactic Acid Co Castor Oil)"; 2009; Pharmaceutical Research; 26(1): 32-39.*

Sokolsky-Papkov et al.; "Long-Acting Poly(DL:Lactic Acid-Castor Oil) 3:7-Bupivacaine Formulation: Effect of Hydrophobic Additives" ; 2011; Pharm. Res.; 28:3265-3273; DOI 10.1007/s11095-011-0497-3 (Year: 2011).*

Graton; "Hydrogen-Bond Accepting Properties of New Heteroaromatic Ring Chemical Motifs: A Theoretical Study"; 2016; J. Chem. Inf. Model.; 56: 322-334 (Year: 2016).*

(Continued)

*Primary Examiner* — Timothy P Thomas
(74) *Attorney, Agent, or Firm* — Baker Hostetler

(57) ABSTRACT

What is disclosed is a semi-solid controlled release pharmaceutical composition containing biocompatible and bio-erodible semi-solid lipid matrix incorporating local anesthetics agents to form a semi-solid solution, a method of using the pharmaceutical composition to treat, and a method of making the pharmaceutical composition.

5 Claims, 7 Drawing Sheets

(56) References Cited

OTHER PUBLICATIONS

Barr et al.; "Post Surgical Pain Management with Poly(ortho esters)"; Advanced Drug Delivery Reviews; Oct. 2002; vol. 54 Issue 7; p. 1041-1048.
Soderberg et al.; "In-vitro release of bupivacaine from injectable lipid formulations investigated by a single drop technique—relation to duration of action in-vivo"; Journal of Pharmacy and Pharmacology; vol. 54 No. 6; 2002; p. 747-755.
Griffin; J. So Cosmetic Chem.; 5:249-35; 1954.
Sokolsky-Papkov et al.; "Poly(DL:Lactic Acid-Castor Oil) 3:7-Bupivacaine Formulation: Reducing Burst Effect Prolongs Efficacy In Vivo"; Journal of Pharmaceutical Sciences; vol. 99 No. 6; Jun. 2010; p. 2732-2738.
Santamaria et al.; "Drug delivery systems for prolonged duration local anesthesia"; Materials Today; vol. 20 No. 1; Jan./Feb. 2017; p. 22-31.
Sokolsky-Papkov et al.; "Long-Acting Poly(DL:Lactic Acid-Castor Oil) 3:7-Bupivacaine Formulation: Effect of Hydrophobic Additives"; Pharmaceutical Research; vol. 28; Jun. 2011; p. 3265-3273.
Soderberg et al.; "The "inverted cup"—A novel in vitro release technique for drugs in lipid formulations"; Journal of Controlled Release; vol. 113; 2006; p. 80-88.
Larsen et al.; "In vivo release of bupivacaine from subcutaneously administered oily solution. Comparison with in vitro release"; Journal of Controlled Release; vol. 81; May 2002; p. 145-154.
International Patent Application No. PCT/US2018/064325; Int'l Search Report and the Written Opinion; dated Mar. 28, 2019; 17 pages.

\* cited by examiner

INJECTABLE LONG-ACTING LOCAL ANESTHETIC SEMI-SOLID FORMULATIONS AND ITS COMPOSITIONS

CROSS-REFERENCE TO RELATED APPLICATIONS

This application is a continuation-in-part of international patent application No. PCT/US2014/019704 filed on Feb. 28, 2014, which claims the benefit of U.S. Provisional Patent Application No. 61/771,011, filed Feb. 28, 2013, the disclosures of which are incorporated herein by reference in their entirety.

TECHNICAL FIELD

What is described herein relates to a semi-solid lipid matrix as a delivery vehicle, and a controlled release semi-solid pharmaceutical composition comprising the semi-solid lipid vehicle and a local anesthetics agent. The pharmaceutical composition can be in the form of an injectable or a topical formulation for controlled delivery of a local anesthetic, which is useful in the treatment of post-operative pain.

BACKGROUND

Systemic morphine administered via patient controlled analgesia (PCA) pumps and oral narcotics are the leading drugs used to treat post-operative pain. These drugs are very effective but have significant side effects, including respiratory depression, nausea, ileus, and a potential for addiction. Due to the addiction potential, these medications are often under-prescribed so that patients continue to experience moderate to severe pain in the immediate post-operative period. Local anesthetics can be used to avoid these side effects. However, the available drugs are very short acting with a maximum of six to eight hours of pain relief. Post-operative pain typically lasts more than two days. A long-acting local anesthetic that could safely release pain medication over two to four days that truly relieve pain without systemic side effects would potentially provide a significant advantage over the leading drugs used to treat post-operative pain.

Much effort has been made to develop sustained or controlled release local anesthetic drug products. These products may be achieved by microencapsulation such as microspheres, microparticles, and implants. The drug delivery vehicle typically consists of a polymeric matrix from which drug is released by diffusion and/or degradation of the matrix.

U.S. Pat. Nos. 6,214,387, 6,921,541, 6,521,259 and 8,221,778 describe preparation and testing of many polymers, such as polyanhydrides, polylactic acid-glycolic acid copolymers and polyorthoesters used as bioerodible matrices for the controlled release of local anesthetics. The active ingredient, a local anesthetic, is typically entrapped or encapsulated in microspheres or microparticles which are then introduced into the surgical cavity via injection, infusion or in the form of implant.

For application such as treatment of post-operative pain, analgesic activity of only a few days would be desirable. Because erosion of poly(DL-lactic acid) is measured in months, and even years, and the erosion time of poly(lactide-co-glycolide) copolymers is measured in weeks to months, these erosion times are clearly not optimal for short term therapy. In addition, the degradation products of these polymers are glycolic acids and lactic acids, which are very acidic and could cause inflammation.

Kim et al., U.S. Pat. No. 8,182,835 describes encapsulating local anesthetics in liposomes, such as multivesicular liposomes, with high encapsulation efficiency and slow drug release in vivo. Liposomal bupivacaine formulations were also investigated, but in vitro releases of less than twelve hours were achieved. Commercial products (e.g., EXPAREL®) were found to reduce mean pain intensity only during the first 24 hours following study drug administration. U.S. Pat. No. 7,053,209 describes a high viscosity liquid controlled delivery system using nonpolymeric esters or mixed esters of one or more carboxylic acids suitable for the delivery of active substances in a controlled fashion. Unfortunately, this system was not able to properly control release bupivacaine, and the drug product based on it only showed pain-relief comparable to the bupivacaine HCl solution commercial product in a phase II trial.

U.S. Pat. Nos. 6,613,355, 6,790,458 and 6,861,068 describes a semi-solid delivery vehicle contains a polyorthoester and an excipient to control release the active ingredients. A long-acting mepivacaine was developed using this semi-solid drug delivery technology. Unfortunately, only about 3 wt % of mepivacaine is able to be loaded into the polyorthoester vehicle due to the drug's low solubility in the vehicle (Barr et al., 2002, Adv Drug Del Rev 54:1041-48). Further, the controlled release of mepivacaine was only extended from two hours to about six hours in rat animal model studies. This drug product showed comparable pain-relief to the bupivacaine HCl solution commercial product in a phase II trial.

While the above systems are useful, their manufacture processes are complicated, cumbersome and expensive. In addition, they are often associated with an initial higher release of drug immediately after injection (also called "burst") followed by inconsistent and poor drug release kinetics, thus lack of reliability in pain relief in animal studies and human trials. There remains a need for controlled release of drugs suitable for pain management.

SUMMARY

One aspect of what is described herein is a pharmaceutical composition consisting of an injectable long-acting local anesthetic semi-solid formulations, comprising i. a semi-solid gel consisting of one or more glycerides having a structure selected from formulas I, II, III, IV, V, or VI

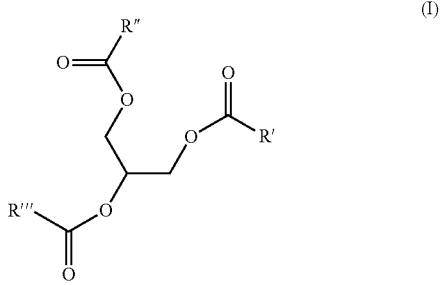

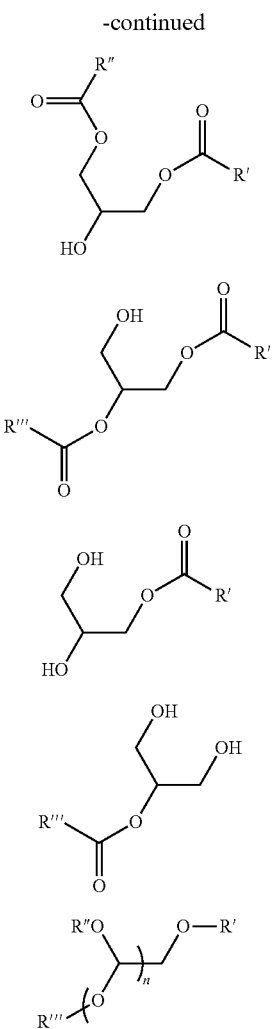

wherein R', R", and R''' are alkyl chains independently consisting of a saturated natural fatty acid comprising 8-22 carbon atoms, a naturally occurring unsaturated fatty acids comprising 16-22 carbons, a non-toxic organic dicarboxylic acid comprising 6-10 carbon atoms, or a naturally occurring omega saturated or unsaturated hydroxy acid, wherein n is 1-10; wherein the mixture of glycerides comprise at least two different alkyl chains, and wherein the mixture of glycerides is at a concentration of 40-99 wt % of the pharmaceutical composition;

ii. a local anesthetic at a concentration of 1-60 wt % of the semi-solid gel, wherein a dose of the pharmaceutical composition comprises an amount of the local anesthetic effective to treat a patient in need thereof, wherein the local anesthetic is fully solubilized in the semi-solid gel;

iii. a first excipient consisting of one or more glycerides having a structure selected from formulas I, II, III, IV, or V, wherein the first excipient is fully miscible with the semi-solid gel and modifies release kinetics of the local anesthetic from the semi-solid gel so that less than 80% of the dose of the local anesthetic is released from the pharmaceutical composition in five days when measured in vitro at 37° C.; and iv. a second excipient consisting of one or more glycerides having a structure selected from formulas I, II, III, IV, or V, wherein the second excipient is fully miscible with the semi-solid gel, wherein the second excipient modifies the viscosity of the pharmaceutical composition to 20-2000 cPs at 30° C.;

wherein the pharmaceutical composition consists of a homogeneous, single phase semi-solid dosage form suitable for injection into the patient.

In one embodiment of the pharmaceutical composition consisting of an injectable long-acting local anesthetic semi-solid formulation, the local anesthetic may be an amide or an ester local anesthetic. The local anesthetic may be one or more of lidocaine, bupivacaine, ropivacaine, mepivacaine, etidocaine, or a fatty acid complex thereof. The local anesthetic preferably is a unit dose for administration to a site in a subject in an amount effective to achieve nerve blockade, local numbness, or pain relief at the site, preferably at a concentration of 1 wt % to 60 wt %, most preferably at a concentration of 5 wt % to 40 wt %.

In another embodiment of the pharmaceutical composition consisting of an injectable long-acting local anesthetic semi-solid formulation, the semi-solid gel comprises polyglyceryl-2-diisostearate, SOFTISAN® 378, SOFTISAN® 645, or SOFTIGEN® 701. The first excipient preferably comprises SOFTIGEN® 701, SOFTISAN® 378, GELUCIRE® 39/01, SUPPOCIRE® A, or SOFTISAN® 138. The first excipient preferably adjusts the rate of release of the local anesthetic from the pharmaceutical composition, has a lower or higher HLB (hydrophobicity) than the semi-solid gel, and is at a concentration of 1 wt % to 50 wt % of the pharmaceutical composition, preferably 5 wt % to 30 wt %, more preferably 10 wt % to 20 wt %, most preferably 0.5 wt % to 5 wt %, and in some cases is 0.5 wt % to 2.5 wt %. The second excipient preferably comprises SOFTIGEN® 701, SOFTISAN® 378, GELUCIRE® 39/01, SUPPOCIRE® A, or SOFTISAN® 138, decreases the viscosity of the pharmaceutical composition, and is at a concentration of 0 wt % to 20 wt % of the pharmaceutical composition. The pharmaceutical composition may further comprise a nonionic surfactant that accelerates dissolution of a depot formed in situ by injection of the pharmaceutical composition into tissue of the patient, at a concentration of 0 wt % to 2.5% of the pharmaceutical composition. The nonionic surfactant may comprise GELUCIRE® 44/14, GELUCIRE® 50/13, LABRAFIL® M1944CS, LABRAFIL® M2125CS, or LABRASOL®.

Another aspect of the description herein is a method for preventing or relieving local pain comprising administering to a subject in need thereof the pharmaceutical composition consisting of an injectable long-acting local anesthetic semi-solid formulations described above. The composition described herein alternatively may be administered by topical application, preferably to skin or mucous membrane. The composition described herein may be administered by injection, such as subcutaneous, intramuscular, or intraperitoneal injection, preferably into the surgical cavity and at different layers within the wound. The pharmaceutical composition is preferably administered by injection by a 21 gauge to a 27 gauge needle. The pharmaceutical composition is preferably injected subcutaneously. For example, when the patient is treated by surgery, the pharmaceutical composition may be injected at the site of the surgery.

Another aspect of the description is a method of manufacturing the pharmaceutical composition consisting of an injectable long-acting local anesthetic semi-solid formulations described above, comprising i. selecting a local anesthetic in a dosage amount sufficient to effectively treat a patient;
ii. fully solubilizing the local anesthetic in a semi-solid gel consisting of one or more glycerides having a structure selected from formulas I, II, III, IV, V, or VI

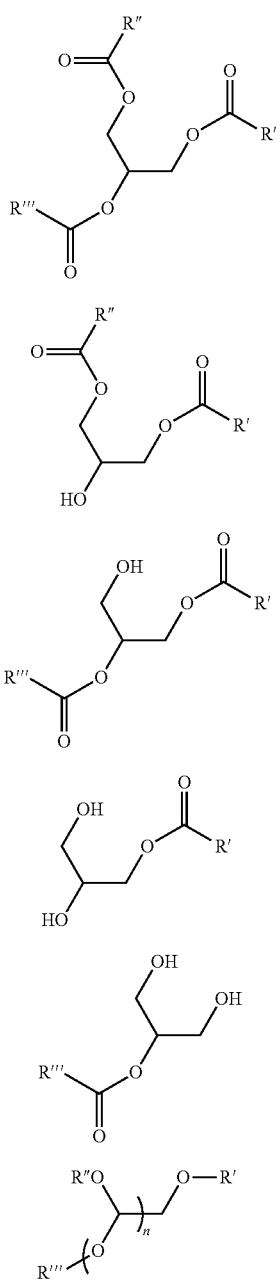

wherein R', R", and R'" are alkyl chains independently consisting of a saturated natural fatty acid comprising 8-22 carbon atoms, a naturally occurring unsaturated fatty acids comprising 16-22 carbons, a non-toxic organic dicarboxylic acid comprising 6-10 carbon atoms, or a naturally occurring omega saturated or unsaturated hydroxy acid, wherein n is 1-10; wherein the mixture of glycerides comprise at least two different alkyl chains, wherein the concentration of the local anesthetic is 1-60 wt % of the semi-solid gel;

iii. measuring the release kinetics of the local anesthetic from the semi-solid gel resulting from step ii to determine if less than 80% of the dose of the local anesthetic is released from the semi-solid gel in five days when measured in vitro at 37° C.;
iv. adding a first excipient to the semi-solid gel resulting from step ii, wherein the first excipient consists of one or more glycerides having a structure selected from formulas I, II, III, IV, or V, having a comparable HLB number than the semi-solid gel, wherein the first excipient is fully miscible with the semi-solid gel and at a concentration sufficient to slow the release of the local anesthetic from the semi-solid gel to less than 80% of the dose of the local anesthetic in five days is at a concentration of 0-20 wt % of the pharmaceutical composition;
v. measuring the viscosity of the local anesthetic semi-solid gel resulting from step iv to determine if the viscosity is less than 2000 cPs at 30° C.; and
vi. adding a second excipient to the semi-solid gel resulting from step iv, wherein the second excipient consists of one or more glycerides having a structure selected from formulas I, II, III, IV, or V, wherein the second excipient is fully miscible with the semi-solid gel, wherein the second excipient modifies the viscosity of the pharmaceutical composition to 20-2000 cPs at 30° C.;

wherein the resulting pharmaceutical composition consists of a homogeneous, single phase dosage form. The method of manufacture may further comprise vii. measuring the rate dissolution of the semi-solid gel in vivo to determine if more than 80% is released in fourteen days; and
viii. adding a nonionic surfactant wherein the nonionic surfactant accelerates the dissolution rate of the semi-solid gel.

The method of manufacture may further comprise selecting a free base or a salt form of the local anesthetic to decrease its dissolution rate from the semi-solid gel to produce a semi-solid gel, wherein less than 80% of the dose of the local anesthetic is released from the semi-solid gel in five days when measured in vitro at 37° C.

DETAILED DESCRIPTION

Advantages of Bioerodible Semi-Solid Depot Technology

Figure 1:
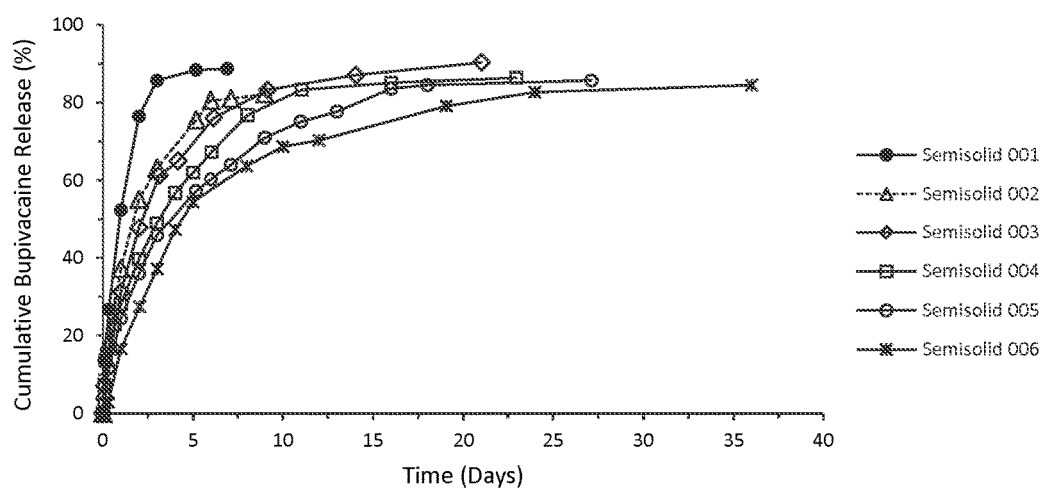
FIG. 1 shows bupivacaine release from a series of different semi-solid compositions containing main lipid carrier with modifying excipients. Semi-solid 001: 5378/bupivacaine (95/5), semi-solid 002: [S378/S701(80/20)]/bupivacaine (92/8), semi-solid 003: [PGDS/G39/01(80/20)]/bupivacaine (95/5), semi-solid 004: [S701/G39/01(90/10)]/bupivacaine/G50/13 (82/9/9), semi-solid 005: [S701/G39/01(80/20)]/bupivacaine (90/10), and semi-solid 006: [S701/G39/01(70/30)]/bupivacaine (90/10). 25 mM phosphate buffered saline, pH 7.4, 37° C.

Biocompatible and Bioerodible Semi-Solid Lipid Depot Containing Bupivacaine

The formulations described herein provide a prolonged period of bupivacaine release such that therapeutic concentrations of the drug are achieved rapidly and maintained for at least 72 hours. The potential benefit of the prolonged release profile is to achieve rapid pain relief, maintaining higher levels of active drug at the site of the pain over time to potentially provide greater relief from pain, and to maintain pain relief for 72 hours following surgery.

The animal model studies described herein demonstrate continuous release of the pain-relieving agent bupivacaine for 72 hours.

Benefits of Bioerodible, Semi-Solid Depot Technology:

No significant initial burst is found in the formulations described herein. Typically, controlled release injections are associated with an initial burst (higher release of drug immediately after injection). In vitro drug release and animal studies have shown that injectables based on our bioerodible semi-solid depot technology produce less post-injection burst that is typically associated with other commercially available injectable controlled release technologies. For example, NUTROPIN® (somatropin of rDNA origin for injection) has a drug release profile of huge burst followed by very slow drug release.

Drug concentration in the semi-solid depot technology described herein can be as high as 40%, considerably greater than what is typical with other controlled release technologies. For example, a long-acting mepivacaine has been developed using this semi-solid drug delivery technology in which only about 3 wt % of mepivacaine can to be loaded into the polyorthoester vehicle due to the drug's low solubility in the vehicle. In addition, the solubility of bupivacaine in typical vegetable oils is less than 3 wt %. The solubility of bupivacaine in olive oil, corn oil, sesame oil, and vegetable oil were determined to be 2.5 wt %, 2.8 wt %, 3.0 wt % and 2.5 wt % respectively.

The semi-solid depot formulations exhibit described herein have very low viscosity, about 10,000 mPa·s or less at 30° C., preferably 1000 mPa·s or less. Therefore, they can be injected through a small needle such as a 23 gauge or even a 25 gauge needle, and will exhibit minimal pain (similar to aqueous solution injection) during injection. Additionally, since the semi-solid formulations described herein have a higher capacity for drug loading, less volume of drug product is required to be injected. Small injection volumes and low viscosity semi-solid formulations result in easier and less painful administration. POE semi-solid formulations have a viscosity of thousands of mPa·s at 30° C., which is difficult to be injected with a 21 gauge needle.

The formulations described herein comprise semi-solid lipids that are glycerides of glycerol with natural fatty acids. These compounds are readily hydrolyzed to glycerol and free fatty acids by lipase. These compounds are non-toxic, and exhibit excellent biocompatibility in the body. The formulations described herein are biodegradable, bioerodible, and fully resorbable. In animal studies, at two weeks after dosing, no adverse effect of the semi-solid formulation on wound healing was observed. The administration site appeared to be pinkish, and the sciatic nerve appeared to be normal, no inflammation, necrosis, ulceration, or infection was observed.

Compared to microspheres and other polymer-based controlled release injectable systems, the semi-solid formulations described herein are readily manufactured at low cost. The active ingredient(s) and semi-solid vehicle components are simply mixed at without the use of solvents at relatively low elevated temperatures. Note that since semi-solid lipid and low-melting point lipid (less than 50° C., and most probably less than 40° C.) (modifying excipient) are used, the manufacturing process can be at about 60° C.

Further, the formulations described herein can be administered directly for site specific delivery. Since the formulations provide a sustained drug release over a period of days to a month resulting in increased duration of pharmacological action, and reduced frequency of drug administration. The formulations also produce reduced side effects (due to local drug delivery) when compared with systemic administration. The ease of use should produce improved patient compliance.

DEFINITIONS

All technical and scientific terms are used herein according to their conventional definitions as they are commonly used and understood by those of ordinary skill in the art of drug delivery. Specific terms for the description herein will be defined below.

The term "semi-solid" denotes the physical state of a material that is flowable under a moderate pressure. More specifically, the semi-solid material has a viscosity of less than 10,000 cps (mPa·s) at 30° C. One of the excipient components can have a viscosity of about 5,000 mPa·s to 6,000 mPa·s. After mixing with a viscosity reducer and active ingredient, the overall viscosity will be reduced to hundreds of cps for the final formulation/drug product.

The term "thixotropic" means a shear thinning property of a fluid or gel material when mixed or agitated. Certain gels or fluids that are thick (viscous) under static conditions will flow (become thin, less viscous) over time when shaken, agitated, or otherwise stressed. They then take a fixed time to return to a more viscous state. Many gels and colloids are thixotropic materials, exhibiting a stable form at rest but becoming fluid when agitated. Thixotropy is the tendency for the viscosity of a liquid to decrease when subjected to shear. Thixotropic Index is the ratio of two viscometer readings. The higher the difference in the two readings, the more thixotropic the material is, and easier to move. The term "thixotropic" is used in its conventional sense to refer to a gel composition that can liquefy or at least exhibit a decrease in apparent viscosity upon application of mechanical force such as shear force. The extent of the reduction is in part a function of the shear rate of the gel when subjected to the shearing force. When the shearing force is removed, the viscosity of the thixotropic gel returns to a viscosity at or near that prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

A "thixotropic agent" as used herein is one that increases the thixotropy of the composition in which it is contained, promoting shear thinning and enabling use of reduced injection force.

The term "bioerodible" refers to a material that gradually decomposes, dissolves, hydrolyzes and/or erodes in situ. Generally, the "bioerodible" semi-solid lipids described herein are materials that are hydrolizable, and bioerode in situ primarily through both lipolysis and hydrolysis.

The semi-solid lipids, solvent and other agents of the description must be "biocompatible"; that is they must not cause irritation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal.

Low-Solubility Semi-Solid Lipids of the Formulation

The semi-solid lipids useful in the formulation described herein are a mixture of one or more monoglycerides, diglycerides, or triglycerides of low water solubility having the structure of I, II, III, IV, V, or low HLB polyglyceryl esters with the structure of VI

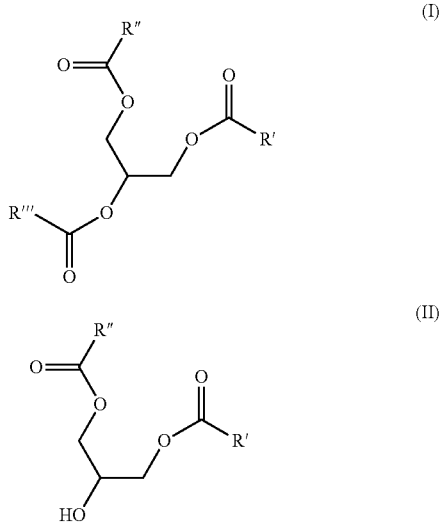

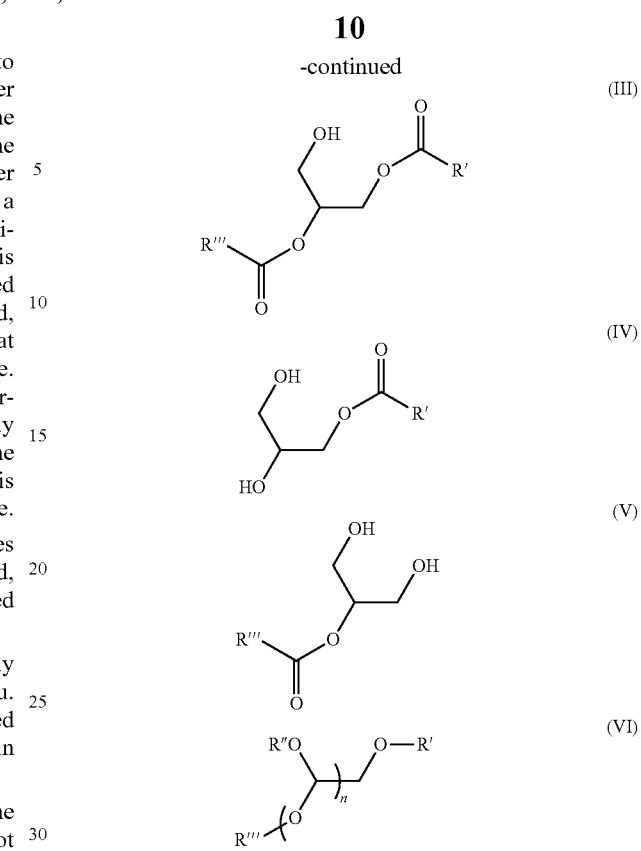

wherein R', R", and R'" are independent fatty acid moiety or hydrogen, and n is 1-10. The fatty acids include saturated natural fatty acids containing 8, 9, 10, 11, 12, 13, 14, 15, 16, 17, 18, 19, 20, 21, or 22 carbon atoms, preferably 8 to 18 carbon atoms, such as caprylic acid, capric acid, lauric acid, myristic acid, palmitic acid, stearic acid, arachidic acid, or behenic acid; or naturally occurring mono-unsaturated fatty acids such as palmitoleic acid, cis-vaccenic acid, or oleic acid; or polyunsaturated fatty acids such as linoleic acid, α-linolenic acid, arachidonic acid, eicosapentaenoic acid, and docosahexaenoic acid; naturally occurring omega saturated and unsaturated hydroxy acids such as 16-hydroxy palmitic acid, 18-hydroxy stearic acid, 2-hydroxy-docosanoic, 15-hydroxy-hexadecanoic acid, 17-hydroxy-octadecanoic acid, 2-hydroxy-oleic acid, 2-hydroxy-linoleic acid, or ricinoleic acid; additional naturally occurring fatty acids such as vernolic acid or furanoid fatty acids; and finally non-toxic organic dicarboxylic acid containing 6, 7, 8, 9 or 10 carbon atoms such as adipic acid, azelaic acid, or sebacic acid which can be used along with other fatty acids. A small portion of these acids can be added to the fatty acid mixtures and react with glycerol to produce the mixed esters.

In addition, polyglyceryl esters with an HLB value of less than 4 and molecular weight of less than 2,000 Dalton (Da), such as polyglyceryl-2-diisostearate (HLB=3.8), polyglyceryl-10-decaoleate (HLB=3.5), or polyglyceryl ester of mixed vegetable fatty acids (HLB=2.5), are also useful semi-solid vehicle.

Triglycerides are typically manufactured through direct esterification of glycerol with defined fatty acid blends and have therefore precise composition and properties (regarding melting point, polarity (hydroxyl value), and consistency). Partial glycerides are esters of glycerol with fatty acids, whereby only a part of the existing hydroxyl groups are esterified. Some hydroxyl groups within the glycerol ester are free contributing to the polar properties of the material.

The semi-solid lipids compositions in the present description comprise triglycerides, diglycerides, and monoglycerides of mixed esters in a relatively viscous liquid or paste form with an aqueous solubility of less than 0.1 mg/mL, with an HLB value of not more than 6, preferably less than 5. Glycerides of short-chain fatty acid with aliphatic chains of fewer than six carbons (i.e., butyric acid) and glycerides of medium-chain fatty acids with aliphatic chains of 6, 7, 8, 9, 10, 11 or 12 carbons are typically in the form of mobile liquid and are difficult to form a long-lasting depot in the human body at the body temperature of 37° C. and physiologic pH. Triglycerides of long-chain fatty acids with aliphatic chains 13, 14, 15, 16, 17, 18, 19, 20 or 21 carbons, and very long chain fatty acids with aliphatic chains longer than 22 carbons typically have a higher melting point and are more likely to be a hard waxy solid at room temperature. As the number of fatty acid carbons increases, the solubility of the formed triglycerides decreases in the human body. Therefore, the triglycerides of mixed esters and partial glycerides of fatty acids useful for the formulation described herein are mixed esters containing medium chain fatty acids. Myristic triglyceride, palmitic triglyceride, and stearic triglyceride are in the form of solid powder or flakes with a melting point of 57° C., 63° C. and/or 71° C., respectively. Fatty acids with aliphatic chains of 6, 7, 8, 9, 10, 11 or 12 carbons, which have high polarity and therefore exhibit superior solvent characteristics for active drugs, and long chain fatty acids with aliphatic chains of 13 to 21 carbons which tends to increase melting point and hardness, so a proper mixed esters containing both medium-chain and long-chain fatty acids can be in the physical form of a soft paste.

There are readily available commercial mixtures of glycerides. For example, SOFTISAN® 378 (S378) is a mixture of caprylic/capric/myristic/stearic triglycerides, containing four types of fatty acids, is an off-white to yellowish soft paste with a drop point of 39° C. to 42° C., and is practically insoluble in water at 20° C. (with a water solubility of less than 0.1 mg/mL). At 40° C., after this material melts and becomes a liquid, it has a dynamic viscosity of 30 mPa·s. For this type of glyceride of saturated fatty acids, the medium-chain fatty acids play the role of solubilizing the active ingredient into the semi-solid lipid, while the hydrophobicity/lipophilicity of long-chain fatty acids is a main factor controlling drug release and controlling the slow erosion/dissolution of semi-solid lipid.

Viscosity also plays a role in controlling the release of active ingredients from the semi-solid depot. Other fatty acids such as omega saturated such as hydroxystearic acid (and unsaturated hydroxy acids) which tends to increase viscosity of the material and other non-toxic organic dicarboxylic acid to increase polarity of the material and solubility of the active drugs. These functional groups such as hydroxyl groups (—OH) and carboxylic groups (—COOH), can form intra and intermolecular hydrogen bonding, and can increase the viscosity of the glycerides of saturated fatty acids. They can also form molecular interactions with drug molecules, and contribute to retain the active ingredient inside the semi-solid depot. For example, caprylic/capric/isostearic/hydroxyl-stearic/adipic glycerides is a mixed ester of a relatively viscous yellowish liquid with a viscosity of approximately 6000 mPa·s at 20° C., and this material is practically insoluble in water (with a water solubility of less than 0.1 mg/mL). Introducing hydroxyl-stearic fatty acid with hydroxyl groups and adipic dicarboxylic acid with carboxylic groups changes this mixed ester into a high viscosity liquid. When additional hydrophobic stearic acid is introduced, the resulting material (caprylic/capric/isostearic/hydroxylstearic/stearic acid/adipic glycerides) becomes a sticky paste with a viscosity of about 540 mPa·s at 50° C.

Unsaturated glycerides with naturally occurring omega unsaturated hydroxy acids, and monounsaturated and polyunsaturated fatty acids typically have a lower melting point and are more likely to be liquid or soft paste. Some hydroxyl groups within the glycerol ester are free contributing to the polar properties of the material, and potential good solubility of active ingredients. Especially, glycerides of unsaturated hydroxy acids show even better solubility for low solubility active ingredients due to the presence of hydroxyl groups. For example, ricinoleic acid partial glycerides is a white to yellowish paste with a viscosity of approximately 500-600 mPa·s at 30° C., and this material is dispersible in water. Other unsaturated partial glyceride examples are glyceryl oleate, glyceryl linoleate, glyceryl linoleate, glyceryl hydroxyoleate, glyceryl hydroxylinoleate, and glyceryl monooleate linoleate, and glyceryl monooleate. Since these materials contain unsaturated components, interaction with oxygen must be considered. Antioxidant(s) may be added to the material to increase stability.

Polyglyceryl esters are formed chemically by esterification of fatty acids, largely saturated or mono-unsaturated, to one or several hydroxyl groups of polyglycerol with the structural formula, VI:

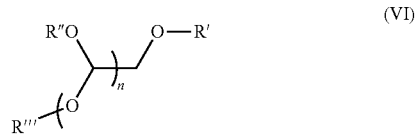

(VI)

where the value of n is not more than 10, preferably less than 4, and R', R", and R'" each may be a fatty acid moiety or hydrogen.

Only 30% to 50% of the total amount of hydroxyl groups typically are esterified by fatty acids. Normally, they are used as emulsifying agents due to their amphiphilic characteristics. Almost all the commercially available polyglyceryl esters are relatively hydrophilic, with a high hydrophilic-lipophilic balance (HLB) value of greater than 4, and are either soluble in water or dispersible in water. They are used as water additives and products, and are not hydrophobic enough to be used as a controlled semi-solid delivery vehicle.

However, polyglyceryl esters such as polyglyceryl-2-diisostearate (HLB=3.8), polyglyceryl-10-decaoleate (HLB=3.5), polyglyceryl ester of mixed vegetable fatty acids (HLB=2.5), bis-diglyceryl polyacyladipate, diglycerin laurate, diglycerin myristate, diglycerin oleate, and polyglyceryl ricinoleate with an HLB value of not more than 4, preferably less than 3, can be used as a semi-solid vehicle component. They can be used as oil additives due to their low hydrophilic-lipophilic balance value, and are fully compatible with semi-solid lipid vehicle components. They typically exist as a viscous liquid due to the presence of multiple hydroxyl groups, and will become a soft paste when a solid lipid was added as a modifying excipient. The molecular weight of the polyglyceryl esters should be less than 2,000 Da, preferably less than 1,500 Da, and most preferably not more than 1,000 Da. For example, polyglyceryl-2-diisostearate (HLB=3.8) is slightly yellow viscous liquid, when a waxy solid lipid G39/01 (a glyceride of $C_{12}$ to $C_{18}$ fatty acids) is added, the mixture becomes a soft paste. Polyglyceryl-10-decaoleate (HLB=3.5) is a viscous liquid, when a waxy solid lipid G39/01 (a glyceride of $C_{12}$ to $C_{18}$ fatty acids) is added, the mixture becomes a soft paste.

The useful semi-solid lipids (triglycerides of mixed esters, partial glycerides (including monoglycerides and diglycerides) of fatty acids, and low HLB polyglyceryl esters) should be hydrophobic enough, and have low solubility with an aqueous solubility of less than 1 mg/mL in physiological pH buffer at 37° C., preferably less than 0.1 mg/mL. They are in the form of either a soft paste, or a viscous liquid at room temperature.

The useful main semi-solid lipids alone, the main semi-solid lipid mixed with the modifying excipients (the final delivery vehicle), and the delivery vehicle with the active ingredients can form a defined long-lasting depot once administered into the body at 37° C., and will gradually degrade/erode, and be dissolved into the body liquids, and the semi-solid lipids will eventually be hydrolyzed to natural free glycerol and free fatty acids by lipase through a process called lipolysis.

The Modifying Excipients

The modifying excipients suitable for the present description are pharmaceutically acceptable and semi-solid lipid compatible materials. These materials can be in the form of liquid, semi-solid, or solid at room temperature, and are fully compatible with the semi-solid lipid to form a single phase semi-solid delivery vehicle for active drugs.

More specifically, suitable modifying excipients can be also triglycerides of mixed esters and partial glycerides of fatty acids as described in the main semi-solid lipid vehicle. Since these modifying excipients are structurally similar to the main semi-solid lipid vehicle, they are expected to be fully compatible. Physically, these materials can be in the form of liquid, semi-solid, or solid at room temperature, and should also have low solubility with an aqueous solubility of less than 1 mg/mL in physiological pH buffer at 37° C., preferably less than 0.1 mg/mL with an HLB value of not more than 6, preferably less than 5. The modifying excipient is preferably to have comparable solubility as the main semi-solid lipid. If the modifying excipient is too hydrophilic and water soluble, it will cause a significant burst of the active drug(s), especially when the active drugs are relatively soluble, which may cause undesirable side effects. If the modifying excipient is significantly more insoluble than the main semi-solid lipid, it will retain in the body significantly longer when the active drug and the main semi-solid lipid is completely dissolved and resorbed by the body.

The purposes of adding modifying excipients to the main semi-solid lipid vehicle is to modify the texture or consistency of the vehicle, to modify the release kinetics of the active drugs from the delivery vehicle, to reduce the viscosity of the main lipid vehicle, and finally to ensure the final drug product/formulation remain as a long-lasting well-defined depot to control the gradual release of active drugs. Any one of the three types of the useful semi-solid lipids, triglycerides of mixed esters, partial glycerides of fatty acids, and low HLB polyglyceryl esters, can be used as a modifying excipient, which will be a mixture of two semi-solid lipids. Another type of useful modifying excipient is a solid triglyceride, diglyceride or monoglyceride with a melting point of less than 60° C., preferably around and slightly above body temperature (35° C. to 50° C.). When the melting point gets too high, it will cause the hardening of the semi-solid vehicle during storage, and this solid triglyceride or partial glycerides could retain the body significantly longer. For example, solid triglycerides and partial glycerides with a melting point of around and slightly above body temperature are typically in the form of waxy solid, and can serve as a lubricant (due to the waxy property from the long alkyl chains of fatty acids) that reduces the viscosity of the relatively viscous liquid or paste. For example, a 10 wt % to 20 wt % of a triglycerides of $C_{10}$ to $C_{18}$ fatty acids (S138), hydrogenated cocoglycerides (a different percentage mixture of $C_{10}$ to $C_{18}$ fatty acids with melting points from 25° C. to 50° C.), glyceryl laurate, glyceryl myristate, glyceryl palmitate, glyceryl monostearate (HLB=5), glyceryl hydroxyl stearate, or a glyceride of $C_{12}$ to $C_{18}$ fatty acids (G39/01, HLB=1) with a melting point of 37° C. to 40° C., a glyceride of $C_{10}$ to $C_{18}$ fatty acids (SUPPOCIRE® A, HLB=1) with a melting point of 35° C. to 36.5° C., glyceryl cocoate (glyceryl monococoate, dicocoate or tricococoate), hydrogenated palm/palm kernel oils (a mixture of monoglycerides, diglycerides and triglycerides with different percentage of $C_{10}$, $C_{12}$, $C_{14}$, $C_{16}$ or $C_{18}$ fatty acids with melting points from 20° C. to 45° C.), can be added to the relatively viscous yellowish liquid of caprylic/capric/isostearic/hydroxylstearic/adipic glycerides (a mixed ester), and changed the delivery vehicle to a relatively non-viscous soft paste. This could not only make the semi-solid depot a more defined shape in the body, and potentially prolong the drug release duration, but also improve the ability of the semi-solid formulation to be administered by syringe.

The concentrations of modifying excipients in the delivery vehicle may vary. For example, the concentration of the excipient in the vehicle may be in the range of about 1 wt % to 50 wt %, preferably about 5 wt % to 30 wt %, and more preferably about 10 wt % to 20 wt %.

Additional further modifying excipients can be added to further modify the properties of the semi-solid drug delivery vehicle. It would be ideal to simply use the main semi-solid lipid alone or in combination with one modifying excipient to form the drug delivery vehicle to meet the drug delivery demands for the active drugs (to achieve the desired drug release profile and duration). However, if needed, another small amount of another pharmaceutically excipient can be used for example to modify the dissolution rate of the vehicle and/or the release kinetics of the active drugs from the delivery vehicle. For example, macrogolglycerides/polyoxylglycerides are mixture of monoesters, diesters and triesters of glycol and monoesters and diesters of PEG (macrogols), which are obtained by partial alcoholysis of vegetable oils with PEG. Suitable excipients include lauroyl polyoxyl-32-glycerides (GELUCIRE® 44/14), stearoyl polyoxyl-32-glycerides (GELUCIRE® 50/13), oleoyl polyoxyl-6-glycerides (LABRAFILL® M1944CS), linoleoyl polyoxyl-6-glycerides (LABRAFILL® M2125CS), lauroyl polyoxyl-6-glycerides (LABRAFILL® M2130CS), caprylocaproyl polyoxyl-8-glycerides (LABRASOL®), and the like. These esters of polyglycolized glycerides can act as a non-ionic solubilizer/emulsifier for the active drugs and semi-solid vehicle. The concentrations of this type of modifying excipients in the delivery vehicle is low, probably in the range of about 0.1 wt % to 10 wt %, preferably about 0.5 wt % to 5 wt %, more preferably about 0.5 wt % to 2.5 wt %.

The Delivery Vehicle of the Formulation Described Herein

The delivery vehicle comprises one main semi-solid lipid, and one or more modifying excipients selected from those described in the preceding section. The delivery vehicle can be prepared by mixing or blending together the main semi-solid lipid and the modifying excipients homogenously. The mixing and blending can be performed by any methods or using any suitable devices to achieve a smooth homogeneous and non-sticky semi-solid mixture at an elevated temperature without the use of any solvents.

Local Anesthetic Semi-Solid Pharmaceutical Compositions

Local anesthetics induce a temporary nerve conduction block, and a local analgesic effect for pain relief in surgical procedures, dental procedures, and injuries.

Clinical local anesthetics belong to one of two classes: amide and ester local anesthetics. Amide local anesthetics include articaine, bupivacaine, cinchocaine/dibucaine, etidocaine, levobupivacaine, lidocaine/lignocaine, mepivacaine, prilocaine, ropivacaine and trimecaine. Ester local anesthetics include benzocaine, chloroprocaine, cocaine, cyclomethycaine, dimethocaine/larocaine, piperocaine, propoxycaine, procaine/novocaine, proparacaine and tetracaine/amethocaine. The local anesthetics may be present as the free base, or as an acid addition salt, or as a mixture thereof. A mixture of two different local anesthetics or a mixture of the same local anesthetics in two forms, the free base form and the acid addition salt, may be used to achieve the desired pharmacological effect and release rate and duration.

The semi-solid injectable form of a local anesthetic of the present description may be prepared by mixing with the delivery vehicle already formed or directly mixed together with the main semi-solid lipid and the modifying excipients. The local anesthetic may be first milled into fine particles before mixing with the other ingredients. The mechanical mixing process is performed at a suitable temperature to completely melt the semi-solid lipid and modifying excipients into a solution, and completely dissolve the active drugs into the delivery vehicle to from a clear solution. Vacuum may be applied to avoid air bubbles, and nitrogen may be applied to reduce oxidation of active drugs and the delivery vehicle components. After achieving a homogeneous and uniform pharmaceutical composition, the local anesthetic semi-solid formulation can be cooled down to ambient temperature.

The amount of local anesthetic present in the composition can vary over a wide range depending on the a number of factors, such as the therapeutically effective dose of the active drug, the desired duration of biological or therapeutic effect, and the release profile of the composition. The concentration of the active agent may be in the range of about 1 wt % to 60 wt %, preferably about 5 wt % to 40 wt %, or more preferably 10 wt % to 40 wt %, most preferably 10 wt % to 30 wt %.

The concentration of the main semi-solid lipid may be in the range of about 40 wt % to 99 wt %, preferably about 50 wt % to 80 wt %, and more preferably about 70 wt % to 80 wt %. The concentration of the first modifying excipient may be in the range of about 1 wt % to 50 wt %, preferably about 5 wt % to 30 wt %, more preferably about 10 wt % to 20 wt %. The concentrations of the second type of modifying excipients may be in the range of about 0.1 wt % to 10 wt %, preferably about 0.5 wt % to 5 wt %, more preferably about 0.5 wt % to 2.5 wt %. In addition, other pharmaceutically acceptable agents such as antioxidants, preservatives, and other inert agents such as coloring or flavoring agents may be added.

This local anesthetic semi-solid pharmaceutical composition of the present description has a smooth non-tacky semi-solid paste. Therefore, the composition can be conveniently applied onto already-open sites such as surgical wounds/site or exposed skin or mucous membrane, or filled into syringes with a 21 to a 25 gauge needle for subcutaneous, intradermal, intramuscular, epidural or intrathecal injection.

After topical application or administration by injection, the active agent is released from the composition in a sustained and controlled manner. The rate of release may be regulated in a variety ways to accommodate the desired duration of therapeutic effect. For example, the rate may be increased or decreased by using different levels of low solubility semi-solid lipids and different levels of low solubility salts of the active agents with acids. It may also be altered by selecting different modifying excipients or by changing their amount, or the combination thereof.

Pharmaceutical Uses

The local anesthetics semi-solid pharmaceutical compositions of the present description can be topically applied onto already-open sites such as skin or mucous membrane, or filled into syringes and directly injected into the surgical cavity and at different layers within the wound, such as across the peritoneal incision and directly below the skin incision. This drug product enables localized treatment of both the incisional and deep visceral pain components normally associated with moderate and major surgery. This drug product provides pain relief for the first three days following surgery when pain is most debilitating. This product has the potential to be widely used to manage post-operative pain following moderate/major surgeries, e.g., abdominal, gynecological, thoracic, or orthopedic surgeries.

Overall Criteria for the Vehicle Components

1. High hydrophobicity and low-solubility

The useful semi-solid lipids (low HLB triglycerides of mixed esters, partial glycerides of fatty acids, and low HLB polyglyceryl esters) should be hydrophobic enough, and have low solubility with an aqueous solubility of less than 1 mg/mL in physiological pH buffer at 37° C., preferably less than 0.1 mg/mL.

2. Semi-solid physical form

They are in the form of either a soft paste, or a viscous liquid at room temperature. Semi-solid material is a third physical form that is intermediate between solid and liquid. These materials do not undergo a physical change when injected, which demands a viscosity low enough so the injection can be performed with a standard needle.

3. Well-defined semi-solid depot at 37° C. after being injected into the body

4. High drug loading

Drug concentration in the semi-solid formulations described herein can be as high as 40%, considerably higher than what is typical with other controlled release technologies.

5. Good compatibility (one single phase semi-solid solution): Similar chemical structures for the semi-solid lipid and modifying excipients.

Main semi-solid lipids: low HLB triglycerides of mixed esters, partial glycerides of fatty acids, and low HLB polyglyceryl esters.

Modifying excipients: 1. same as main semi-solid lipids; 2. solid triglycerides (specific melting point range; or 3. pharmaceutically acceptable non-ionic solubilizers/emulsifiers.

6. Biocompatible, bioerodible and fully resorbable
7. Non-toxic (safety)

EXAMPLES

1. Preparation of Pharmaceutical Compositions

The semi-solid local anesthetic pharmaceutical compositions below were prepared as follows: The local anesthetics, semi-solid lipid, and modifying excipients were added to a glass container, and then heated to about 60° C. to 95° C. depending on the properties of local anesthetics and the vehicle components used to completely melt semi-solid lipid and modifying excipients into a solution, and completely dissolve the active drugs into the delivery vehicle to from a clear solution while mixing. After achieving a homogeneous and uniform pharmaceutical composition, the local anesthetic semi-solid formulation can be cooled down to ambient temperature naturally.

60 wt % of S378: 40 wt % of tetracaine/lidocaine (1:2)

After heating to 60° C., all components were melted, and the two local anesthetics were dissolved to form a clear solution and became a semi-transparent soft paste after cooling down to room temperature.

85 wt % of S378: 15 wt % of lidocaine/bupivacaine (2:1)

After heating to 90° C., all components were melted, and the two local anesthetics were dissolved to form a clear solution and became a whitish soft paste after cooling down to room temperature.

60 wt % of S701: 40 wt % of lidocaine/bupivacaine (3:1)

After heating to 60° C., all components were melted, and the two local anesthetics were dissolved to form a clear solution and became a transparent slightly viscous liquid after cooling down to room temperature.

90 wt % of S701/G39/01 (4:1): 10 wt % of bupivacaine

After heating to 90° C., all components were melted, and the local anesthetic was dissolved to form a clear solution and became a semi-transparent soft paste after cooling down to room temperature.

80 wt % of S645: 20 wt % of lidocaine

After heating to 90° C., all components were melted, and the local anesthetic was dissolved to form a clear solution and became a transparent slightly viscous liquid after cooling down to room temperature.

75 wt % of S645: 25 wt % of lidocaine/bupivacaine (4:1)

After heating to 90° C., all components were melted, and the local anesthetic was dissolved to form a clear solution and became a transparent slightly viscous liquid after cooling down to room temperature.

The following commercial products were used, which are available in GMP quality and quantity.

| | |
|---|---|
| SOFTISAN ® 378 (S378) | caprylic/capric/myristic/stearic triglycerides |
| SOFTISAN ® 645 (S645) | caprylic/capric/isostearic/hydroxyl-stearic/adipic glycerides, mixed esters |
| SOFTIGEN ® 701 (S701) | ricinoleic acid partial glycerides |
| GELUCIRE ® 39/01 (G39/01) | glycerides of C12-C18 fatty acids |
| GELUCIRE ® 44/14 (G44/14) | lauroyl polyoxyl-32-glycerides |
| GELUCIRE ® 50/13 (G50/13) | steroyl polyoxyl-32-glycerides |
| PGDS | polyglyceryl-2-diisostearate |

2. In Vitro Release

Preparation of Semi-Solid Pharmaceutical Compositions

The semi-solid local anesthetic semi-solid pharmaceutical compositions below were prepared as follows: The local anesthetics, semi-solid lipid, modifying excipients, and fatty acids (oleic acid and palmitic acid) used to complex with bupivacaine were added to a glass container, and then heated to about 80° C. to 95° C. to completely melt semi-solid lipid and modifying excipients into a solution, and completely dissolve the active drugs into the delivery vehicle to from a clear solution while mixing. After achieving a homogeneous and uniform pharmaceutical composition, the local anesthetic semi-solid formulation was then cooled down to ambient temperature naturally. The semi-solid formulations described herein appeared as a semi-transparent or opaque soft paste.

semi-solid 001: S378/bupivacaine (95/5) or (95 wt %/5 wt %)

semi-solid 002: [S378/S701(80/20)]/bupivacaine (92/8)

semi-solid 003: [PGDS/G39/01(80/20)]/bupivacaine (95/5)

semi-solid 004: [S701/G39/01(90/10)]/bupivacaine/G50/13 (82/9/9)

semi-solid 005: [S701/G39/01(80/20)]/bupivacaine (90/10)

semi-solid 006: [S701/G39/01(70/30)]/bupivacaine (90/10)

semi-solid 005A: S701/bupivacaine (90/10)

semi-solid 003A: [PGDS/G39/01(30/70)]/bupivacaine (95/5)

semi-solid 003B: [PGDS/G39/01(50/50)]/bupivacaine (95/5)

semi-solid 003C: [PGDS/G39/01(70/30)]/bupivacaine (95/5)

semi-solid 003D: [PGDS/G39/01(90/10)]/bupivacaine (95/5)

semi-solid 007A: [S645/G39/01(90/10)]/bupivacaine (95/5)

semi-solid 007B: [S645/G39/01(80/20)]/bupivacaine (95/5)

semi-solid 005M1: [S701/G39/01(80/20)]/bupivacaine (95/5)

semi-solid 005M2: [S701/G39/01(80/20)]/bupivacaine (86/14)

semi-solid bupivacaine OA: S378/bupivacaine OA: (80/20)

semi-solid bupivacaine PA: S378/bupivacaine PA: (80/20)

3. Bupivacaine Solubility:

The solubility of bupivacaine in typical vegetable oils is less than 3 wt %. The solubility of bupivacaine in olive oil, corn oil, sesame oil, and vegetable oil were determined to be 2.5 wt %, 2.8 wt %, 3.0 wt % and 2.5 wt % respectively.

a. Vegetable oil: 2.0 g of vegetable oil and 20.5 mg of bupivacaine were combined and completely dissolved with stirring for 40 minutes. An additional 20.7 mg of bupivacaine was added and completely dissolved in 40 minutes with stirring. An additional 21.0 mg of bupivacaine was added and approximately 10 g dissolved with stirring for 3 hours. The total amount of dissolved Bupivacaine was approximately 51.2 mg. The solubility in vegetable oil was determined to be (51.2 mg/2000 mg)*100=2.5 wt %.

b. Olive oil: A similar procedure as in a) was conducted with olive oil. The total amount of dissolved bupivacaine was 20.7+20.4+10.0≈51.1 mg, and the solubility of bupivacaine in olive oil was determined to be (51.1 mg/2000 mg)*100=2.5 wt %.

c. Corn oil: A similar procedure as in a) was conducted with corn oil. The total amount of dissolved bupivacaine was 20.7+20.0+15.0≈55.7 mg, and the solubility of bupivacaine in corn oil was determined to be (55.7 mg/2000 mg)*100=2.8 wt %.

d. Sesame oil: A similar procedure as in a) was conducted with corn oil. The total amount of dissolved bupivacaine was 19.8+20.0+20.0≈59.8 mg, and the solubility of bupivacaine in sesame oil was determined to be (59.8 mg/2000 mg)*100=3.0 wt %.

4. In Vitro Drug Release

For in vitro release determination, about 50 mg of each semi-solid formulation was weighed and enclosed in a porous semi-permeable membrane, and then placed into glass bottles with screw caps. 100 mL of 25 mM phosphate saline buffer (PBS), pH 7.4 was added to each bottle. The test bottles were transferred to a 37° C. oven without agitation. At various time points, bottles were removed and samples of about 1 mL were removed and analyzed for local anesthetic bupivacaine content by light absorption at 220 nm. 49 mL of the buffer in each test bottle was removed and replaced with 50 mL of fresh buffer so that the PBS in each bottle was maintained at 100 mL.

The drug release profiles of all the listed semi-solid compositions are summarized in the FIGS. 1 to 7.

Mechanism for Controlled Release of the Formulations Described Herein

When the lipophilic semi-solid formulation is placed into an aqueous environment, water will diffuse into the semi-solid lipid matrix, the active agent on the formulation surface will first gradually dissolve into the surrounding aqueous media. As water penetrates into the semi-solid lipid matrix/depot, the semi-solid lipid vehicle erodes, both by surface and bulk erosion, and gradually dissolve into the surrounding aqueous media, the active agent inside the matrix/depot will also gradually diffuse out and will be released into the surrounding aqueous media, thus the active ingredient is released from the semi-solid matrix/depot in a sustained and controlled manner.

Factors that Affect the Drug Release Rate

The release rate of active agent is affected both by the semi-solid lipid vehicle components and the active ingredient, and can be regulated in a variety ways to accommodate the desired duration of therapeutic effect.

For the semi-solid lipid vehicles, the release rate of active agent can be increased or decreased by using different levels/amounts/ratios of low solubility semi-solid lipid vehicles with different water solubilities and dissolution rates. As water solubility and dissolution rate of the semi-solid lipids decrease, it will take longer for the semi-solid lipid depot to be dissolved and absorbed, thus resulting longer duration of drug release as long as the active agent exhibits sufficient low solubility.

This semi-solid lipid vehicle can employ one single low solubility semi-solid lipid, if this semi-solid lipid alone can achieve the desired duration of therapeutic effect. The main low solubility semi-solid lipid needs to be compatible with the active agent, and needs to have good solubility for the active agent so that sufficient drug loading can be achieved for the desired duration of therapeutic effect.

In many cases, two or more low solubility semi-solid lipids need to be used as the drug delivery vehicle. A secondary lipid component can be added to the main semi-solid lipid vehicle in an effort to adjust the release rate of active agent. Again, this additional lipid component also needs to be compatible and soluble toward the active agent. In addition, this additional lipid component can be used to modify the viscosity of the semi-solid lipid vehicle, and the texture and consistence of the drug delivery vehicle and the final drug product.

The semi-solid lipid vehicle(s) including the main lipid vehicle and the modifying vehicle will mainly determine the duration of drug release and how long the vehicle will be completely eroded and dissolved in vivo. Furthermore, a small percentage of third modifying excipient a can be added to further fine-tune the drug release rate, and erosion and dissolution rate of the semi-solid lipid vehicle.

For the active pharmaceutical ingredient, in order to develop a long-acting local anesthetic drug product, one first need to select an appropriate local anesthetic drug for the targeted indication, since there are about twenty local anesthetics available (e.g., benzocaine, chloroprocaine, cocaine, cyclomethycaine, dimethocaine/larocaine, piperocaine, propoxycaine, procaine/novocaine, proparacaine, tetracaine/amethocaine, lidocaine, articaine, bupivacaine, cinchocaine/dibucaine, etidocaine, levobupivacaine, lidocaine/lignocaine, mepivacaine, prilocaine, ropivacaine, and trimecaine), and each drug has their own physical and chemical properties, water solubility, potency, and suitable indications. The selected drug needs to be compatible with the semi-solid lipid vehicle components, so that sufficient drug can be loaded into the delivery vehicle and there should be no chemical reactions between the active agent and the vehicle components, and the drug itself is stable during manufacturing, processing, and storage.

Once the drug is selected, then the form with low water solubility, preferably lower than 0.1 mg/mL, will be employed since a lot of drugs can be in the form of free base or free acid, or salt forms. For example, bupivacaine can be in the form of a free base or a salt such as bupivacaine hydrochloride which is widely marketed in commercial products under various trade names, including MARCAIN™, MARCAINE™, SENSORCAINE® and VIVACAINE®. The hydrochloride (HCl) salt of bupivacaine has a water solubility of 600 mg/mL (BASF MSDS sheet), while the free base form of bupivacaine has a predicted water solubility of 0.0977 mg/mL (DrugBank data). In addition, if there is a need to further decrease the water solubility of the drug bupivacaine, one can convert the bupivacaine into a salt with fatty acids and other low solubility acids.

Bupivacaine can be readily converted to a salt with saturated or unsaturated fatty acids such as lauric acid, myristic acid, palmitic acid, and oleic acid. Other low solubility non-toxic organic acids such as pamoic acid can also be used. This conversion can not only further reduce bupivacaine water solubility, but also increase its compatibility and solubility in the semi-solid vehicle. bupivacaine can be converted into a salt in advance before being incorporated into the semi-solid vehicle, or can be added into the semi-solid vehicle simultaneously at a 1:1 molar ratio during the formulation manufacturing process.

For example, the solubility of bupivacaine in S378 was approximately 5 wt %. However, the solubility of bupivacaine oleic acid (or other fatty acids) in S378 was increased up to more than 20 wt %. In addition, the release rate and duration of the semi-solid (S378) formulation containing bupivacaine oleic acid is expected to be significantly slower and longer than the semi-solid (S378) formulation containing bupivacaine. As the drug fatty acid complex solubility decreases, the drug release duration will be significantly longer.

As shown in FIG. 1, semi-solid composition 001 to 006 containing approximately 5 wt % bupivacaine up to 10 wt % showed a good controlled release from days to a month. Five out of the six semi-solid compositions employed either one or two (one major semi-solid lipid with a modifying lipid) semi-solid lipids as the delivery vehicle, one of them employed a third modifying excipient, which is a solubilizer/non-ionic surfactant, G50/13. As the overall hydrophobicity of the formulation depots increase, their water solubility decrease, and thus resulting slower dissolution rate and longer drug release duration.

Figure 2:
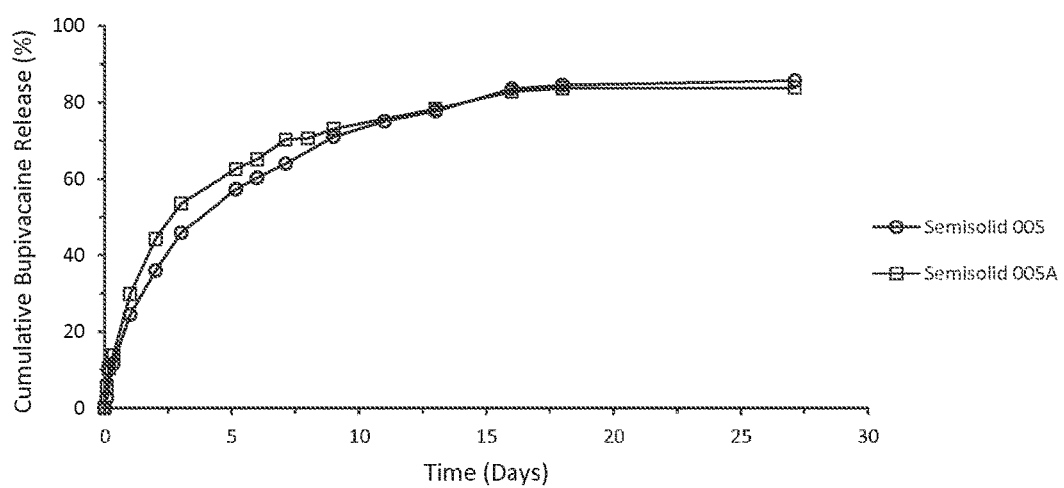
FIG. 2 shows bupivacaine release from one single semi-solid lipid (S701) and this semi-solid lipid modified with an additional lipid. Semi-solid 005: [S701/G39/01(80/20)]/bupivacaine (90/10), semi-solid 005A: S701/bupivacaine (90/10). 25 mM phosphate buffered saline, pH 7.4, 37° C.

FIG. 2 showed bupivacaine release from two similar semi-solid compositions, semi-solid 005: [S701/G39/01(80/20)]/bupivacaine (90/10), and semi-solid 005A: S701/bupivacaine (90/10). Modifying excipients can modify the release kinetics of the drug. Semi-solid 005 and 005A (with only one semi-solid lipid) both contained approximately 10 wt % bupivacaine. When about 20 wt % of G39/01 was added to S701, the mixture become a slightly harder paste, and the overall hydrophobicity/lipophilicity of the mixture vehicle increased due to the higher lipophilicity of G39/01, therefore, the release rate of bupivacaine decreased although the release duration of the two formulations is very close.

Figure 3:
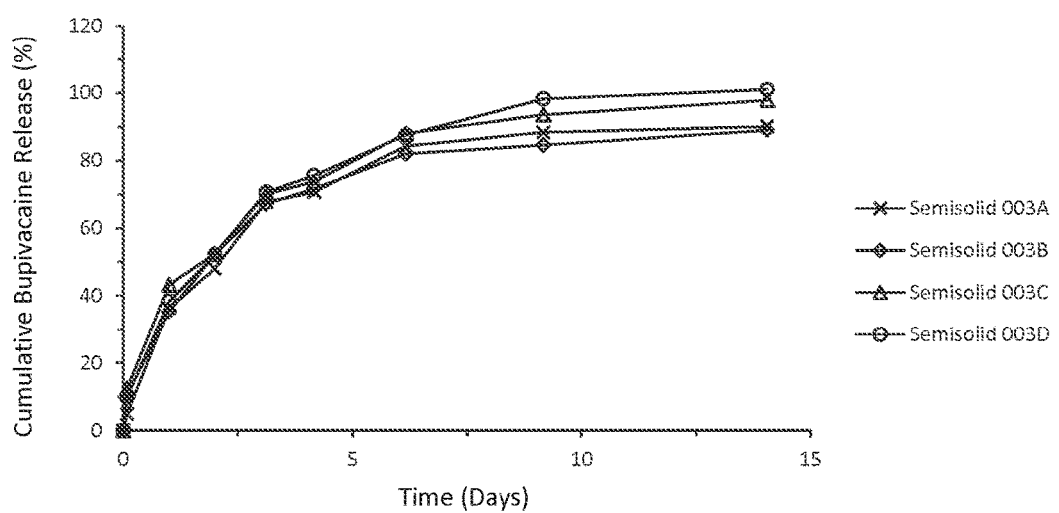
FIG. 3 shows bupivacaine release from four different ratios of two semi-solid lipid components: semi-solid 003A: [PGDS/G39/01(30/70)]/bupivacaine (95/5), semi-solid 003B: [PGDS/G39/01(50/50)]/bupivacaine (95/5), semi-solid 003C: [PGDS/G39/01(70/30)]/bupivacaine (95/5), semi-solid 003D: [PGDS/G39/01(90/10)]/bupivacaine (95/5). 25 mM phosphate buffered saline, pH 7.4, 37° C.

FIG. 3 showed bupivacaine release from four different ratios of two semi-solid lipid components, PGDS/G39/01 (30/70), PGDS/G39/01(50/50), PGDS/G39/01(70/30), PGDS/G39/01(90/10)]. All four compositions contained approximately 5 wt % bupivacaine. When these two components were mixed at different ratios, it yielded a very soft paste to relatively waxy hard paste as the component of G39/01 increase from 10 wt % to 70 wt %. The semi-solid composition 003A and 003B produced very similar drug release profile, and the semi-solid composition 003C and 003D produced very similar drug release profile. Therefore, different semi-solid consistency (soft paste vs. hard paste) can be made depending on their applications.

Figure 4:
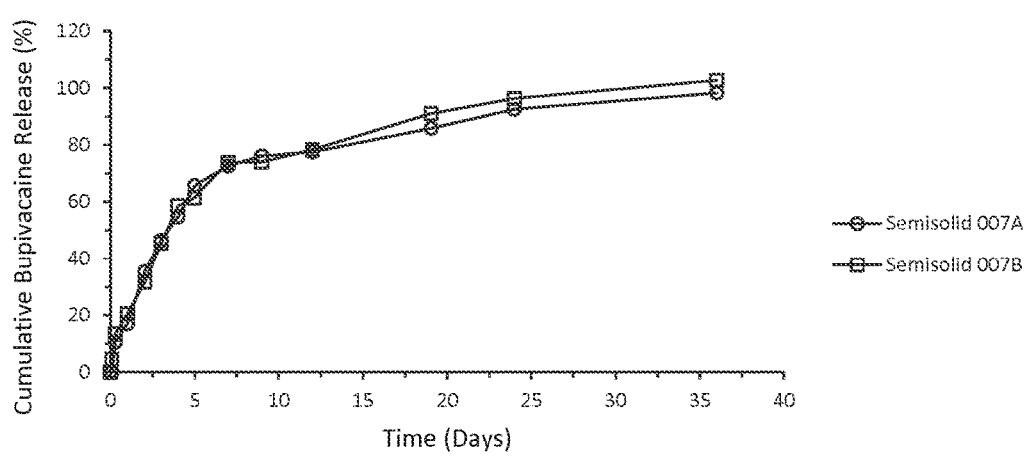
FIG. 4 shows bupivacaine release from two different ratios of two semi-solid lipid components: semi-solid 007A: [S645/G39/01(90/10)]/bupivacaine (90/5), semi-solid 007B: [S645/G39/01(80/20)]/bupivacaine (95/5). 25 mM phosphate buffered saline, pH 7.4, 37° C.

FIG. 4 showed bupivacaine release from two different ratios of two semi-solid lipid components, S645/G39/01(90/10) and S645/G39/01(80/20). Both semi-solid compositions, semi-solid 007A and semi-solid 007B, contained approximately 5 wt % bupivacaine. 5645 is a yellowish high-viscosity liquid material, when 10 wt % to 20 wt % of G39/01 is added, both semi-solid compositions, semi-solid 007A and semi-solid 007B, yielded very close bupivacaine release profile. Adding 10 wt % and 20 wt % of G39/01 to S645 reduced the viscosity of the formulation from 2454 cPs (for neat S645) to 1546 cPs (37% reduction of viscosity) and 1002 cPs (59% reduction of viscosity) respectively, and make the semi-solid formulations more readily injectable.

Figure 5:
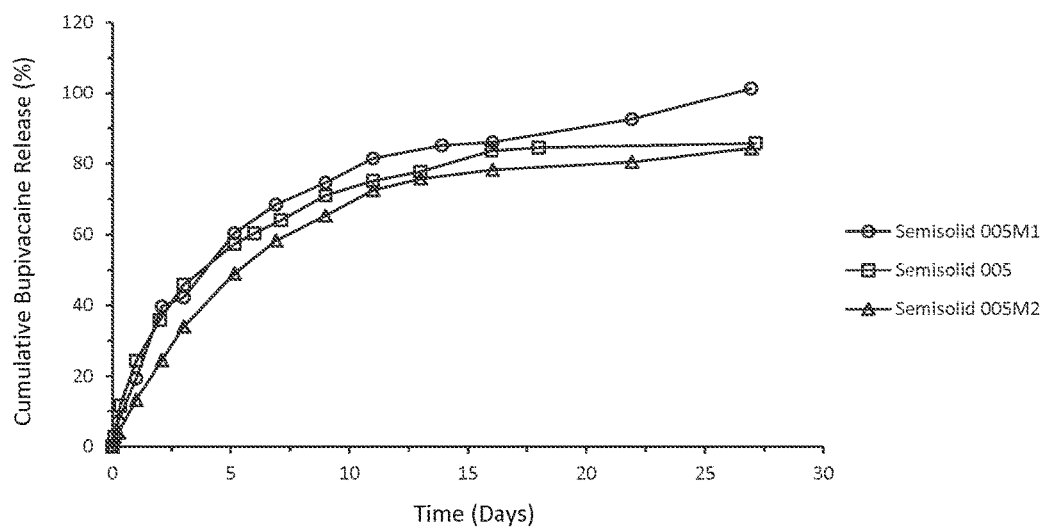
FIG. 5 shows bupivacaine release from the same two semi-solid lipid component vehicle at three different drug loading levels, approximately 5 wt %, 10 wt %, and 14 wt % bupivacaine respectively: semi-solid 005M1: [S701/G39/01(80/20)]/bupivacaine (90/5), semi-solid 005: [S701/G39/01(80/20)]/bupivacaine (90/10), and semi-solid 005M2: [S701/G39/01(80/20)]/bupivacaine (86/14). 25 mM phosphate buffered saline, pH 7.4, 37° C.

FIG. 5 showed bupivacaine release from the same two semi-solid lipid component vehicle, S701/G39/01(80/20), at three different drug loading levels, approximately 5 wt %, 10 wt %, and 14 wt % bupivacaine respectively. As the drug loading increases, the bupivacaine release rate decreases.

Figure 6:
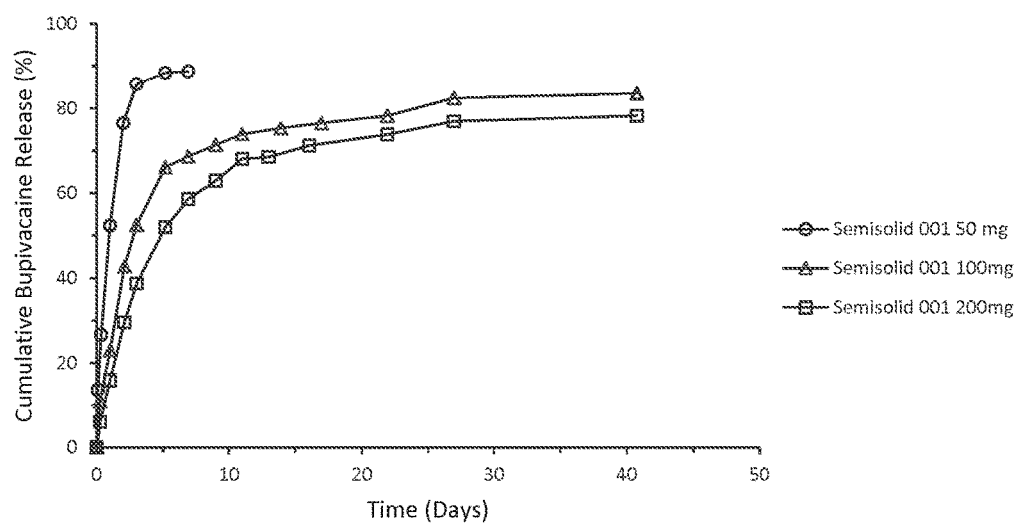
FIG. 6 shows bupivacaine release from three different amounts and volumes (50, 100, and 200 mg) of a semi-solid formulation: S378/bupivacaine (95/5) in 25 mM phosphate buffered saline, pH 7.4, 37° C.

FIG. 6 showed bupivacaine release from three different amounts/volumes, 50 mg, 100 mg, and 200 mg of the same semi-solid formulation, S378/bupivacaine (95/5). As the amounts/volumes of the formulation increases, the release rate of bupivacaine relative to the total drug loading decreases as it take longer time for the drug to diffuse out and the vehicle to erode, and thus the total drug release duration is significantly longer.

Figure 7:
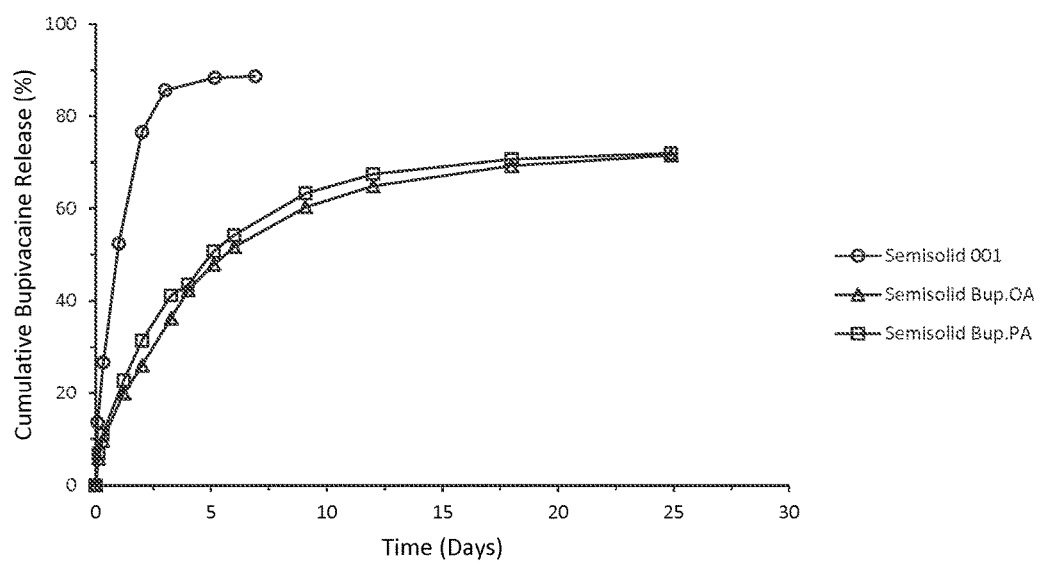
FIG. 7 shows bupivacaine and bupivacaine fatty acid complex release from the same semi-solid lipid vehicle, one containing bupivacaine base, semi-solid 001: S378/bupivacaine (95/5); the other two containing bupivacaine and fatty acid complexes, bupivacaine with oleic acid and palmitic acid formulations, semi-solid bupivacaine OA: S378/bupivacaine OA: (80/20), semi-solid bupivacaine PA: S378/bupivacaine PA: (80/20). 25 mM phosphate buffered saline, pH 7.4, 37° C.

FIG. 7 showed bupivacaine and bupivacaine fatty acid complex release from the same semi-solid lipid vehicle S378. Semi-solid 001 contains approximately 5 wt % bupivacaine, while semi-solid bupivacaine OA: S378 and semi-solid bupivacaine PA both contains approximately 20 wt % bupivacaine and oleic acid and palmitic acid.

The solubility of bupivacaine in S378 was only at approximately 5 wt % level. However, the solubility of bupivacaine oleic acid and palmitic acid complexes increased to about 20 wt %. In addition, the release rate and duration of the semi-solid (S378) formulation containing bupivacaine oleic acid and palmitic acid is significantly slower and longer than the semi-solid (S378) formulation containing bupivacaine due to the decreased water solubility of bupivacaine fatty acid complex.

Viscosity Determination

This purpose of the viscosity measurement for the semi-solid formulations is to demonstrate that our semi-solid formulations has the feature of very low viscosity, and are readily injectable through a 23 gauge to a 21 gauge needle.

Viscosity Determination Procedure:

The viscosity of the semi-solid formulations were determined on a calibrated Brookfield RVDV-I Prime CP model viscometer using cone spindle CPE-51. The semi-solid formulation samples stored in sealed glass vials were first heated to about 40° C. to 50° C. in an oven until the samples became a flowable viscous liquid. Then approximately 0.5 gram of each sample was weighed into the center the warmed sample cup. Avoid bubbles when possible. Attach the sample cup to the viscometer, and measure the viscosity at an appropriate speed of rotation so that the percentage torque is between 10% and 100%. Record the viscosity and percentage torque at the target temperature. Due to the soft paste nature of these materials at room temperature, the viscosity of semi-solid formulations was determined at 30° C. at that point the semi-solid formulations become a flowable viscous liquid/semi-solid under pressure.

Viscosity Values for the Semi-Solid Formulations Used in In Vitro Release Studies Temperature typically has a strong effect on the semi-solid formulations, and these formulations exhibit significant decreasing viscosity with an increase in temperature. At ambient temperature, the semi-solid formulations appear as a soft paste, and their viscosity are often too high. For the semi-solid formulation of [PGDS/G39/01(70/30)]/bupivacaine (95/5), its viscosity was 5000 mPa·s at 28° C. before the semi-solid formulation was melted. When the semi-solid formulation was melted at 30° C., the semi-solid formulation's viscosity was only 88 mPa·s. For the semi-solid formulation vehicle [S701:G39/01(90/10)], when the temperature was increased from 25° C. to 30° C., its viscosity decreased from 2548 to 445 mPa·s as the semi-solid vehicle became melted. For the S645 neat vehicle, its viscosity decreased from 6000 mPa·s to 3650 mPa·s when temperature increased from 20° C. to 35° C.

The viscosity results for the semi-solid formulations listed in the in vitro release study were summarized in Table 1. The viscosity value of these semi-solid formulations ranges from 73 cPs to 1528 cPs, with the majority of them below 1000 cPs at 30° C. Centipoise (cP) and milliPascal seconds (mPa·s) are the CGS and SI units for viscosity. 1 cP=1 mPa·s. The viscosity of all the semi-solid formulations was measured at 30° C.

TABLE 1

Viscosity results for semi-solid formulations

| Sample ID | Semi-solid formulation composition | Viscosity (cP) at 30° C. |
|---|---|---|
| semi-solid 001 | S378/bupivacaine (95/5) or (95 wt %/5 wt %) | 44 |
| semi-solid 002 | [S378/S701(80/20)]/ bupivacaine (92/8) | 73 |
| semi-solid 003 | [PGDS/G39/01(80/20)]/ bupivacaine (95/5) | 252 |
| semi-solid 004 | [S701/G39/01(90/10)]/ bupivacaine /G50/13 (82/9/9) | 408 |
| semi-solid 005 | [S701/G39/01(80/20)]/ bupivacaine (90/10) | 600 |

TABLE 1-continued

Viscosity results for semi-solid formulations

| Sample ID | Semi-solid formulation composition | Viscosity (cP) at 30° C. |
|---|---|---|
| semi-solid 006 | [S701/G39/01(70/30)]/ bupivacaine (90/10) | 1000 |
| semi-solid 003A | [PGDS/G39/01(30/70)]/ bupivacaine (95/5) | 88 |
| semi-solid 003B | [PGDS/G39/01(50/50)]/ bupivacaine (95/5) | 125 |
| semi-solid 003C | [PGDS/G39/01(70/30)]/ bupivacaine (95/5) | 186 |
| semi-solid 003D | [PGDS/G39/01(90/10)]/ bupivacaine (90/5) | 310 |
| semi-solid 005A | S701/bupivacaine (90/10) | 615 |
| semi-solid 005M1 | [S701/G39/01(80/20)]/ bupivacaine (95/5) | 1095 |
| semi-solid 005M2 | [S701/G39/01(80/20)]/ bupivacaine (86/14) | 491 |
| semi-solid 007A | [S645/G39/01(90/10)]/ bupivacaine (95/5) | 1528 |
| semi-solid 007B | [S645/G39/01(80/20)]/ bupivacaine (95/5) | 983 |

2. Low-Viscosity Semi-Solid Formulations

The viscosity values for the main components of the semi-solid vehicle are relatively low, typically below 1000 cPs at 30° C., except for S645, which is a very viscous liquid. The viscosity values of the four main semi-solid components were determined at 30° C. and summarized in Table 2.

TABLE 2

Viscosity values of the main components of the semi-solid vehicle

| Sample ID | Viscosity (cP) at 30° C. |
|---|---|
| S378 neat | 45 |
| S701 neat | 563 |
| S645 neat | 2454 |
| PGDS neat | 427 |

The semi-solid drug delivery vehicle typically contains two or more components, the main semi-solid component with one or two modifying excipients. The overall semi-solid vehicle typically exhibits even lower viscosity, since the modifying excipient often acts as a waxy lubricant, thus further reducing the viscosity of semi-solid vehicle when compared with the main semi-solid component. The viscosity values for the four main components modified with 10 wt % or 20 wt % of G39/01 were determined and summarized in Table 3. For the first main semi-solid lipid S378, the viscosity remained at very low viscosity at about 50 cPs after being modified with 10 wt % or 20 wt % of G39/01. For the second main semi-solid lipid S701, the viscosity of the overall semi-solid vehicle reduced from 563 cPs (for neat S701) to 445 cPs and 383 cPs respectively after being modified with 10 wt % and 20 wt % of G39/01. For the third main semi-solid lipid S645, the viscosity of the overall semi-solid vehicle reduced from 2454 cPs (for neat S645) to 1546 cPs (37% reduction of viscosity) and 1002 cPs (59% reduction of viscosity), respectively, after being modified with 10 wt % and 20 wt % of G39/01. For the fourth main semi-solid lipid PGDS, the viscosity of the overall semi-solid vehicle reduced from 427 cPs (for neat PGDS) to 321 cPs and 238 cPs respectively after being modified with 10 wt % and 20 wt % of G39/01.

TABLE 3

Viscosity values for the overall semi-solid vehicle (main component + modifying excipient)

| Sample ID | Viscosity (cP) at 30° C. |
|---|---|
| S378:G39/01 (90/10) | 53 |
| S378:G39/01 (80/20) | 57 |
| S701:G39/01 (90/10) | 445 |
| S701:G39/01 (80/20) | 383 |
| S645:G39/01 (90/10) | 1546 |
| S645:G39/01 (80/20) | 1002 |
| PGDS:G39/01 (90/10) | 321 |
| PGDS:G39/01 (80/20) | 238 |

Once the active ingredient, bupivacaine, was incorporated into the final semi-solid drug delivery vehicle through a hot melt process, the mixture formed a semi-solid solution formulation with the active drug molecularly dispersed in the semi-solid vehicle media. Again, the overall semi-solid formulations typically exhibit very lower viscosity (below 1000 cPs). The active ingredient can also affect the viscosity of the semi-solid formulations. The active drug can act as a plasticizer and/or a lubricant, and further reduce the viscosity of the semi-solid formulations when compared with the semi-solid vehicle. However, as the drug (solid powder) loading (especially above 40 wt % level) increases, the soft semi-solid paste formulation can change to a relatively hard semi-solid paste formulation.

For the first two semi-solid formulations using 5378 as the main semi-solid lipid component, the viscosity remained at very low viscosity between 50 and 70 cPs after incorporating approximately 5 wt % of the solid bupivacaine powder. For the second two semi-solid formulations using S701 as the main semi-solid lipid component, the viscosity increased from 445 cPs and 383 cPs to 468 cPs and 600 cPs, respectively, after incorporating approximately 10 wt % of the solid bupivacaine powder. For the third two semi-solid formulations using 5645 as the main semi-solid lipid component, the viscosity of the semi-solid formulations remained almost unchanged when compared with the semi-solid vehicle after incorporating approximately 5 wt % of solid bupivacaine powder. For the fourth two semi-solid formulations using PGDS as the main semi-solid lipid component, the viscosity of the semi-solid formulations increased somewhat when compared with the semi-solid vehicle after incorporating approximately 5 wt % of solid bupivacaine powder.

All six semi-solid formulations using S378, S701, and PGDS as the main semi-solid lipid components with the viscosity ranging from 55 cPs to 600 cPs at 30° C. are readily injectable with mechanical pressure (shear force) with a 23 gauge needle, while the two semi-solid formulations using S645 as the main semi-solid lipid component are readily injectable with a 21 gauge needle (still injectable with a 23 gauge needle with some resistance), thanks to the waxy property from the long alkyl chains of fatty acids from the semi-solid lipid components.

TABLE 4

Viscosity values for the final semi-solid formulations (overall semi-solid vehicle + bupivacaine)

| Sample ID | Viscosity (cP) at 30° C. |
|---|---|
| [S378/S701(90/10)]/bupivacaine (95/5) | 55 |
| [S378/S701(80/20)]/bupivacaine (95/5) | 71 |

TABLE 4-continued

Viscosity values for the final semi-solid formulations
(overall semi-solid vehicle + bupivacaine)

| Sample ID | Viscosity (cP) at 30° C. |
|---|---|
| [S701/G39/01(90/10)]/bupivacaine (90/10) | 468 |
| [S701/G39/01(80/20)]/bupivacaine (90/10) | 600 |
| [S645/G39/01(90/10)]/bupivacaine (95/5) | 1528 |
| [S645/G39/01(80/20)]/bupivacaine (95/5) | 983 |
| [PGDS/G39/01(90/10)]/bupivacaine (95/5) | 252 |
| [SPGDS/G39/01(80/20)]/bupivacaine (95/5) | 310 |

In Vivo Rat Sciatic Nerve Block Tests

Male rats weighing between 200 g and 350 g were used to assess the duration of nerve conduction block, which induced by each of the different semi-solid formulations had been tested. The rats were handled daily and habituated to the testing paradigm for at least 60 minute prior to examination. Sensory and motor blockade were examined as described below. In addition to sensory testing, motor testing was performed at each time point to examine the ability of the rats to move their hind leg by gait posture and paw placing. Animals were handled and cared in compliance with institutional, state, and federal animal welfare regulation. The protocol was approved by IACAC.

All rats were anesthetized with 3.5% to 4.0% isoflurane in oxygen and maintained with 1.5%-2.0% isoflurane. 0.5 cc of antibiotic solution (800,000 units/mL penicillin G sodium) was injected to prevent infection. Under aseptic condition, the left thigh area was shaved and an incision was made on the upper ⅓ portion. The thigh muscles were gently dissected by blunt dissection to expose the sciatic nerve. Semi-solid formulations were placed adjacent to the sciatic nerve under direct vision in the fascia plane deep to the hamstrings and the site. The most superficial fascia layer was closed with a single suture. The edges of the outer skin were approximated and closed with surgical staples. For all rats, drug-containing semi-solid formulations were implanted on the left side of sciatic nerve.

Hot-Plate Measurement:

For each time-point, the rat was put on 56° C. hot-plate (cut-off time is 15 seconds) and the latency of lifting the hind paw was recorded (for both paws of the animal) for five times with intervals at least 20 seconds. The highest and lowest readings were discarded and the average of middle three readings was used as the final reading for the particular time-point.

Motor Blockade Measurement:

1. Paw Placing:

For both paws, the animals were held gently by a trained researcher and the dorsal paw, one at a time, was slowly slide over a edge of test platform until reach the toes for 5 times. At each time, if the rat successfully places its testing paw onto the surface of the platform, it was scored as 1 (therefore, the maximum score is 5 for each paw) and as 0 if it fails.

2. Paw Motor Ability Measurement:

A 4-point scale system was used:

(1) normal appearance.
(2) intact dorsiflexion, but impaired splaying toes when elevating the tail of rat.
(3) completely plantar flexion without splaying ability.
(4) number 3 plus impaired gait.

The paw motor ability assessment was used for each time-point as well.

For both paws, the animals were held gently by a trained researcher dorsally.

Dissection

At two week time points following the administration, and the surgical site skin was examined to observe if any affection on wound healing. Then after, the sites where the semi-solid formulation was administered were re-opened and examined visually by naked eyes under anesthesia. After the examination was finished, the rats were euthanized by $CO_2$.

1. 88 wt % of [S701/G39/01(9/1)]: 10 wt % of bupivacaine: 2 wt % G44/14:

This semi-solid formulation was prepared as described in the preceding section. For all rats, sensory blockage lasted for a period of 72 hours with maximum block intensity (latency=12.5 sec) at 4 hour post-administration. Motor blockade lasted for approximately 4 hours with the densest motor block seen at 2 hour post-administration. Paw placing returns to normal at 6 hour post-administration. At two weeks after dosing, no adverse effect of the semi-solid formulation on wound healing was observed. The administration site appeared to be pinkish, and the sciatic nerve appeared to be normal, no inflammation, necrosis, ulceration, or infection was observed. In addition, minimal depot residue was observed at the administration site.

2. 88 wt % of [S701/G39/01(9/1)]: 10 wt % of bupivacaine: 2 wt % G50/13:

This semi-solid formulation was prepared as described in the preceding section. For all rats, sensory blockage lasted for a period of 72 hours with maximum block intensity (latency=15.0 sec) at 4 hour post-administration. Motor blockade lasted for approximately 4 to 6 hours with the densest motor block seen at 2 hour post-administration. Paw placing returned to normal at about 6 hour post-administration. At two weeks after dosing, no adverse effect of the semi-solid formulation on wound healing was observed. The administration site appeared to be pinkish, and the sciatic nerve appeared to be normal, no inflammation, necrosis, ulceration, or infection was observed. In addition, minimal depot residue was observed at the administration site.

3. 85 wt % of [S701/G39/01(9/1)]: 10 wt % of bupivacaine: 5 wt % G50/13:

This semi-solid formulation was prepared as described in the preceding section. For all rats, sensory blockage lasted for a period of 72 hours with maximum block intensity (latency=15.0 sec) at 4 hour post-administration. Motor blockade lasted for approximately 4 hours with the densest motor block seen at 2 hour post-administration. Paw placing returns to normal at about 6 hour post-administration. At two weeks after dosing, no adverse effect of the semi-solid formulation on wound healing was observed. The administration site appeared to be pinkish, and the sciatic nerve appeared to be normal, no inflammation, necrosis, ulceration, or infection was observed. In addition, minimal depot residue was observed at the administration site.

4. 80 wt % of [S645/G43/01(85/15)]: 20 wt % of lidocaine oleic acid:

This semi-solid formulation was prepared as described in the preceding section. For all rats, sensory blockage lasted for a period of 72 hours with maximum block intensity (latency=14.2 sec) at 4 hour post-administration. Motor blockade was not observed. Paw placing returned to normal at about 6 hour post-administration. At two weeks after dosing, no adverse effect of the semi-solid formulation on wound healing was observed. The administration site appeared to be pinkish, and the sciatic nerve appeared to be normal, no inflammation, necrosis, ulceration, or infection was observed. In addition, minimal depot residue was observed at the administration site.

The present description having been thus described, modifications and variations of the molecular structures, proportions of the various components in the semi-solid delivery vehicle or pharmaceutical composition, method of manufacture and other parameters of the description thereof as would be apparent to those of skill in the art will be understood to be within the scope of the appended claims.

What is claimed is:

1. A pharmaceutical composition consisting of
  5-14% bupivacaine,
  63-76% a mixture of ricinoleic acid partial glycerides (S701), and
  17-27% a mixture of C12-C18 fatty acids (G39/01);
wherein the pharmaceutical composition consists of a biocompatible, bioerodible, homogeneous, semi-solid gel; and wherein the semi-solid gel consists of a soft paste with a viscosity of 408-1095 cPs at 30° C., and forms a depot in an aqueous buffer that releases less than 80% of the bupivacaine in five days when measured in vitro at 37° C.

2. The pharmaceutical composition of claim 1 consisting of
  72% S701,
  18% G39/01, and
  10% bupivacaine.

3. The pharmaceutical composition of claim 1 consisting of
  63% S701,
  27% G39/01, and
  10% bupivacaine.

4. The pharmaceutical composition of claim 1 consisting of
  76% S701,
  19% G39/01, and
  5% bupivacaine.

5. The pharmaceutical composition of claim 1 consisting of
  69% S701,
  17% G39/01, and
  14% bupivacaine.

* * * * *